United States Patent [19]
Yokota et al.

[11] Patent Number: 5,089,650
[45] Date of Patent: Feb. 18, 1992

[54] PROCESS FOR PRODUCING CARBONIC ACID ESTER

[75] Inventors: Shigeru Yokota; Hiroshi Koyama; Hidetaka Kojima, all of Himeji, Japan

[73] Assignee: Daicel Chemical Industries, Ltd., Osaka, Japan

[21] Appl. No.: 91,884

[22] Filed: Sep. 1, 1987

[30] Foreign Application Priority Data

Sep. 12, 1986 [JP] Japan ............................ 61-215178
Sep. 12, 1986 [JP] Japan ............................ 61-215179

[51] Int. Cl.$^5$ ...................... C07C 69/96; C07C 68/00
[52] U.S. Cl. ........................... 558/277; 558/260; 558/274; 558/265
[58] Field of Search ............... 558/277, 274, 260, 265

[56] References Cited

U.S. PATENT DOCUMENTS

| | | | |
|---|---|---|---|
| 3,846,468 | 11/1974 | Perrotti et al. | 558/277 X |
| 3,963,586 | 6/1976 | Ginnasi et al. | 558/277 |
| 3,980,690 | 9/1976 | Cipriani et al. | 558/277 |
| 3,994,960 | 11/1976 | Yamazaki et al. | 558/277 X |
| 4,218,391 | 8/1980 | Romano et al. | 558/277 |
| 4,285,882 | 8/1981 | Kramer et al. | 560/124 X |
| 4,305,890 | 12/1981 | Kramer et al. | 558/260 |
| 4,370,275 | 1/1983 | Stammann et al. | 558/277 |
| 4,388,247 | 6/1983 | Kramer et al. | 558/260 |
| 4,636,576 | 1/1987 | Bhattacharya et al. | 558/277 |
| 4,638,076 | 1/1987 | Bhattacharya | 558/277 |

FOREIGN PATENT DOCUMENTS 0220863  5/1987  European Pat. Off.
2160524 12/1985 United Kingdom.

OTHER PUBLICATIONS

Roberts et al., Basic Principles of Organic Chemistry W. A. Benjamin, Inc., N.Y., 1964, pp. 1196 and 1210.

Primary Examiner—Jose G. Dees
Attorney, Agent, or Firm—Flynn, Thiel, Boutell & Tanis

[57] ABSTRACT

Disclosed herein is a process for producing a carbonic acid ester by reacting alcohol, carbon monoxide, and oxygen with one another in the presence of a copper compound alone or together with a platinum group metal compound and a reaction accelerator, characterized in that (I) the reaction is carried out in a nitrile compound or amide compound as a solvent, (II) the reaction is carried out in the presence of a reaction accelerator which consists of a quaternary phosphonium halide and a quaternary phosphonium weak acid salt or quaternary phosphonium alkoxide, and/or (III) the reaction is carried out in the presence of a quinoid compound or a compound that changes into a quinoid compound under the reaction conditions.

16 Claims, No Drawings

PROCESS FOR PRODUCING CARBONIC ACID ESTER

BACKGROUND OF THE INVENTION

1. Field of the Invention

The present invention relates to a process for producing a carbonic acid ester. A carbonic acid ester is an industrially important compound as an intermediate and solvent for the production of polymers and drugs and agricultural chemicals.

2. Description of the Prior Art

A carbonic acid ester is industrially produced by the reaction of an alcohol with phosgene. This process, however, has a disadvantage that phosgene is highly toxic and the reaction of an alcohol with phosgene produces highly corrosive hydrochloric acid as a by-product.

There is a process for producing a carbonic acid ester without using phosgene. According to this method, an alcohol, carbon monoxide, and oxygen are reacted with one another in the presence of a copper compound alone or together with a platinum group metal compound and a basic compound. (See Japanese Patent Publication Nos. 11129/1970 and 8816/1986 and Japanese Patent Laid-open No. 185542/1983.) This process also has a disadvantage in that the catalyst, especially the copper component, is poor in solubility and the formation of the carbonic acid ester is rather slow. It has an additional disadvantage in that a large amount of carbon dioxide as a by-product is formed as the result of the combustion of carbon monoxide and the decomposition of carbonic acid ester.

SUMMARY OF THE INVENTION

It is an object of the present invention to provide a new process for producing a carbonic acid ester with a minimum of carbon dioxide being formed as a by-product. This new process does not have the disadvantages of poor solubility and low reaction rate. The gist of the present invention resides in a process for producing a carbonic acid ester by reacting an alcohol, carbon monoxide, and oxygen with one another in the presence of a copper compound alone or together with a platinum group metal compound and a reaction accelerator, characterized in that (I) the reaction is carried out in a nitrile compound or amide compound as a solvent, (II) the reaction is carried out in the presence of a reaction accelerator which consists of a quaternary phosphonium halide and a quaternary phosphonium weak acid salt or quaternary phosphonium alkoxide, and/or (III) the reaction is carried out in the presence of a quinoid compound or a compound that changes into a quinoid compound under the reaction conditions.

DETAILED DESCRIPTION OF THE INVENTION

The materials used in the process of the present invention are described in detail in the following.

The platinum group metal compound includes halides, acetates, and nitrates of ruthenium, rhodium, and palladium. Of these platinum group metal compounds, a palladium salt is most desirable. Usually the platinum group metal compound is used in an amount of 0.1 to 1000 mmol, preferably 1 to 100 mmol, for 1 liter of alcohol.

The copper compound includes cuprous and cupric halides, acetates, and nitrates Usually these copper compounds are used in an amount of more than 1 mol, preferably more than 3 mol, per 1 mol of the platinum group metal compound.

The alcohol as a reactant in the process of the invention includes saturated aliphatic alcohols such as methanol and ethanol: unsaturated aliphatic alcohols such as allyl alcohol: aromatic alcohols such as phenol; and diols and polyols. Preferable among them are those having 1 to 20 carbon atoms. Particularly preferable is methanol.

The carbon monoxide and oxygen may be used in the pure form or in the diluted form. A diluent in the latter case may be argon or carbon dioxide which is inert in the reaction. Air may be used as the oxygen. The reaction is carried out under normal pressure or appropriate pressure. Carbon monoxide and oxygen are introduced into the reaction system such that their partial pressures are 0.1-30 atm. and 0.05-10 atm., respectively.

The reaction accelerator includes trialkylamines, heterocyclic crosslinked amines, di-substituted-carbodiimides, alkali metal salts, and alkali metal alkoxides (which are basic substances described in Japanese Patent Publication No. 8816/1986), and quaternary phosphonium compounds.

According to the present invention, the reaction is carried out in the presence of any of the above-mentioned substances (I), (II), and (III). The reaction is described in detail in the following.

Reaction that employs (I):

According to the present invention, a nitrile compound or amide compound is used as a solvent in the production of a carbonic acid ester by the reaction of alcohol, carbon monoxide, and oxygen which is carried out in the presence of a copper compound alone or together with a platinum group metal compound and reaction accelerator.

The nitrile compound includes benzonitrile and isobutyronitrile, and the amide compound includes N,N-dimethylformamide and N,N-dimethylacetamide. These solvents may be used individually or in combination with one another. In addition, the solvents should preferably have a boiling point higher than that of water and the carbonic acid ester to be produced. Such solvents make it possible to recycle the catalyst in the form of a liquid or a slurry to the reaction system in the step (such as flash vaporization) of separating the catalyst from the resulting carbonic acid ester and water.

The total amount of the solvent in the reaction liquid should be 5–80% by volume, preferably 10–50% by volume. With an amount in excess of 80% by volume, the concentration of the reactant is so low that the reaction rate is slow. With an amount less than 5% by volume, the reactants are not dissolved completely.

The nitrile compound or amide compound used as a solvent increases the efficiency of the copper compound and hence increases the production rate of carbonic acid ester.

Reaction that employs (II):

According to the present invention, a carbonic acid ester is produced through the reaction of alcohol, carbon monoxide, and oxygen in the presence of (a) a copper compound alone or together with a platinum group metal compound, (b) a quaternary phosphonium halide, and (c) a quaternary phosphonium weak acid salt or quaternary phosphonium alkoxide.

The quaternary phosphonium halide used in the present invention is represented by the formula (1) below.

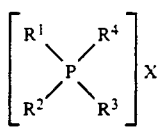

where $R^1$, $R^2$, $R^3$, and $R^4$ denote alkyl groups (e.g., methyl, ethyl, and butyl), alkoxyl groups, aryl groups (e.g., phenyl), aryloxy groups, substituted alkyl groups, substituted alkoxy groups, substituted aryl groups, and substituted aryloxy groups. They may be the same or different. X denotes a halogen such as chlorine, bromine, and iodine.

Examples of the quaternary phosphonium halide include [(n-Bu)$_4$P]Cl, [(n-Bu)$_3$CH$_3$P]Cl, [(n-Pr)$_4$P]Cl, [(n-Bu)$_4$P]Br, and [(n-Pr)$_4$P]Br (Bu: butyl group, Pr: propyl group).

The quaternary phosphonium halide is used in an amount of 0.05 wt % to saturation in the reaction liquid if it is a solid, and in an amount of 0.05 wt % to the amount of solvent if it is a liquid. The optimum amount depends on the rate of formation of carbonic acid ester and carbon dioxide.

The quaternary phosphonium weak acid salt used in the present invention is represented by the formula (2) below.

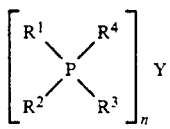

where $R^1$, $R^2$, $R^3$, and $R^4$ are defined as in the formula (1); Y denotes an anion of a carboxylic acid or carbonic acid; and n is a numeral equal to the valence of the anion.

Examples of the quaternary phosphonium weak acid salt include those compounds which are represented by the formulas below.

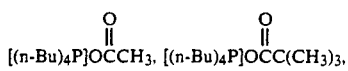

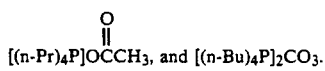

The quaternary phosphonium alkoxide is a compound represented by the formula (2) above, in which $R^1$, $R^2$, $R^3$, and $R^4$ are defined as in the quaternary phosphonium weak acid salt; n is 1; and Y denotes an alkoxyl group. Examples of the quaternary phosphonium alkoxide include those compounds which are represented by [(n-Bu)$_4$P]OCH$_3$ and (n-Bu)$_4$P]OC$_2$H$_5$.

The quaternary phosphonium weak acid salt or the quaternary phosphonium alkoxide is used in an amount of 0.05 wt % to saturation in the reaction liquid if it is a solid, and in an amount of 0.05 wt % to the amount of solvent if it is a liquid. The optimum amount depends on the rate of formation of carbonic acid ester and carbon dioxide.

The reaction of alcohol, carbon monoxide, and oxygen in the presence of the copper compound alone or together with the platinum group metal compound, quaternary phosphonium halide, and quaternary phosphonium weak acid salt or quaternary phosphonium alkoxide is advantageous over the reaction in the presence of the catalyst system disclosed in Japanese Patent Publication No. 8816/1986 in that the formation of carbon dioxide as a by-product is greatly reduced. The catalyst system of the invention is a little slower in reaction rate than that disclosed in said Japanese Patent. However, the reaction rate can be readily increased by raising the reaction temperature and the oxygen partial pressure and also by using a proper solvent. Decreasing the side reactions and increasing the selectivity for carbonic acid ester are desirable because the unreacted reactants can be recycled.

Reaction that employs (III):

According to the present invention, a carbonic acid ester is produced through the reaction of alcohol, carbon monoxide, and oxygen in the presence of a quinoid compound or a compound which changes into a quinoid compound under the reaction conditions.

Examples of the quinoid compound include unsubstituted or substituted ortho- or para-benzoquinones (having a substituent cyano, carboxymethyl, and methyl group) polynuclear quinones such as anthraquinone; heterocyclic quinones; and their imino, N-alkyl, or N-arylimino derivatives.

Examples of the compound which changes into a quinoid compound under the reaction conditions include ketals of the corresponding quinoid compounds and hydrogenated compounds thereof, such as hydroquinone.

The quinoid or the compound which changes into a quinoid under the reaction conditions should be used in an amount of 0.1 to 5 wt % for the total amount of the reactants.

The reaction system may contain a third component such as alkali metal salt disclosed in Japanese Patent Publication No. 8816/1986.

The quinoid or the compound which changes into a quinoid under the reaction conditions suppresses the formation of carbon dioxide as a by-product and produces a carbonic acid ester advantageously.

To further illustrate the invention, and not by way of limitation, the following examples are given.

COMPARATIVE EXAMPLE 1

In a 500-ml jacketed flask equipped with a stirrer and condenser were placed 221 ml of methanol, 3.76 mmol of palladium bromide, 16.4 mmol of cuprous bromide, 7.51 mmol of potassium bromide, and 22.5 mmol of potassium acetate. Reaction was carried out at 60° C for 2 hours while carbon monoxide and oxygen were being introduced into the flask under normal pressure at a flow rate of 8.0 liters/hour and 4.0 liters/hour, respectively.

The analysis by gas chromatography of the liquid product indicated that dimethyl carbonate (DMC) formed at a rate of 285 mmol/liter-hour ($r_{DMC}$).

EXAMPLES 1 TO 4

The same procedure as in Comparative Example 1 was repeated except that a nitrile compound as a solvent was used and the amount of methanol was changed as shown in Table 1. Dimethyl carbonate was formed at a rate ($r'_{DMC}$) which is 1.74 times or above greater than that ($r_{DMC}$) in Comparative Example 1.

TABLE 1

| Example | Amount of methanol (ml) | Amount of solvent (ml) | r'$_{DMC}$ (mmol/L-h) | r'$_{DMC}$/r$_{DMC}$ |
|---|---|---|---|---|
| 1 | 110.5 | Benzonitrile 110.5 | 495 | 1.74 |
| 2 | 166 | Benzonitrile 55 | 495 | 1.74 |
| 3 | 199 | Benzonitrile 22 | 505 | 1.77 |
| 4 | 110.5 | Isobutyronitrile 110.5 | 508 | 1.78 |

It is noted from Table 1 that the nitrile solvent greatly increases the rate at which DMC is formed.

EXAMPLES 5 AND 6

The same procedure as in Comparative Example 1 was repeated except that an amide compound as a solvent was used and the amount of methanol was changed as shown in Table 2. Dimethyl carbonate was formed at a rate (r'$_{DMC}$) which is 1.46 times or above greater than that (r$_{DMC}$) in Comparative Example 1.

TABLE 2

| Example | Amount of methanol (ml) | Amount of solvent (ml) | r'$_{DMC}$ (mmol/L-h) | r'$_{DMC}$/r$_{DMC}$ |
|---|---|---|---|---|
| 5 | 199 | Dimethylformamide 22 | 417 | 1.46 |
| 6 | 199 | Dimethylacetamide 22 | 430 | 1.51 |

It is noted from Table 2 that the amide solvent greatly increases the rate at which DMC is formed.

COMPARATIVE EXAMPLE 2

The same procedure as in Example 6 was repeated except that the solvent was replaced by 22 ml of xylene, which is disclosed in Japanese Patent Publication No. 8816/1986. Dimethyl carbonate was formed at a rate of 348 mmol/liter-hour. This is 1.22 times higher than that in Comparative Example 1. This result suggests that xylene is less effective than nitrile compounds and amide compounds in increasing the rate at which DMC is formed.

COMPARATIVE EXAMPLE 3

In the same apparatus as used in Comparative Example 1 were placed 221 ml of methanol, 1.88 mmol of palladium chloride, 8.18 mmol of cuprous chloride, 3.76 mmol of tetra-n-butylphosphonium chloride, and 11.3 mmol of tetra-n-butylphosphonium acetate Reaction was carried out at 60° C. for 1 hour while carbon monoxide and oxygen were introduced into the flask at normal pressure and a flow rate of 8.0 liters/hour and 4.0 liters/hour, respectively. Dimethyl carbonate was formed at a rate of 93.7 mmol/liter-hour.

EXAMPLE 7

The same procedure as in Comparative Example 3 was repeated except that the amount of methanol was changed to 99 ml and 22 ml of benzonitrile was added. Dimethyl carbonate was formed at a rate of 128 mmol/liter-hour, which is 1.37 times greater than that in Comparative Example 3. This suggests that the nitrile compound also effectively increases the rate at which DMC is formed in the reaction that employs the catalyst system composed of copper, palladium, and phosphonium.

COMPARATIVE EXAMPLE 4

In a 500-ml jacketed flask equipped with a stirrer and condenser were placed 221 ml of methanol, 1.88 mmol of palladium chloride, 3.76 mmol of potassium chloride, 8.18 mmol of cuprous chloride, and 11.3 mmol of potassium acetate. Reaction was carried out at 60° C. for 1 hour while carbon monoxide and oxygen were introduced into the flask at normal pressure and a flow rate of 8.0 liters/hour and 4.0 liters/hour, respectively.

The liquid product and offgas were analyzed by gas chromatography. The results are shown in Table 3, in which r(DMC) and r(CO$_2$) represent the rate at which dimethyl carbonate and carbon dioxide were formed, respectively, and S(CO$_2$) represents the percentage of carbon dioxide formed as a by-product which is defined as follows:

$$\frac{r(CO_2)}{r(DMC) + r(CO_2)} \times 100$$

EXAMPLE 8

The same procedure as in Comparative Example 4 was repeated except that the potassium chloride was replaced by 3.76 mmol of tetra-n-butylphosphonium chloride and the potassium acetate was replaced by 11.3 mmol of tetra-n-butylphosphonium chloride. Results of the analysis are shown in Table 3.

TABLE 3

| Example | r(DMC) [mmol/L-h] | r(CO$_2$) [mmol/L-h] | S(CO$_2$) (%) |
|---|---|---|---|
| Comparative Example 4 | 160 | 45.6 | 22.2 |
| Example 8 | 93.7 | 9.36 | 9.1 |

COMPARATIVE EXAMPLE 5

In the same apparatus as used in Comparative Example 4 were placed 188 ml of methanol, 33 ml of benzonitrile, 3.76 mmol of palladium bromide, 7.51 mmol of potassium bromide, 16.4 mmol of cuprous bromide, and 22.5 mmol of potassium acetate. Reaction was carried out at 60° C. for 1.5 hours while carbon monoxide and oxygen were being introduced into the flask at normal pressure and a flow rate of 20.0 liters/hour and 10.0 liters/hour, respectively. The results of analyses are shown in Table 4.

EXAMPLE 9

The same procedure as in Comparative Example 5 was repeated except that the potassium bromide was replaced by 7.51 mmol of tetra-n-butylphosphonium bromide and the potassium acetate was replaced by 22.5 mmol of tetra-n-butylphosphonium acetate. The results of analyses are shown in Table 4.

TABLE 4

| Example | r(DMC) [mmol/L-h] | r(CO$_2$) [mmol/L-h] | S(CO$_2$) (%) |
|---|---|---|---|
| Comparative Example 5 | 435 | 378 | 46.4 |
| Example 9 | 340 | 169 | 33.2 |

COMPARATIVE EXAMPLE 6

The same procedure as in Comparative Example 5 was repeated except that the potassium acetate was replaced by 2.5 mmol of potassium benzoate. The results of analyses are shown in Table 5.

EXAMPLE 10

The same procedure as in Example 9 was repeated except that the tetra-n-butylphosphonium acetate was replaced by 22.5 mmol of tetra-n-butylphosphonium benzoate. The results of analyses are shown in Table 5.

TABLE 5

| Example | r(DMC) [mmol/L·h] | r(CO2) [mmol/L·h] | S(CO2) (%) |
| --- | --- | --- | --- |
| Comparative Example 6 | 443 | 348 | 44.0 |
| Example 10 | 192 | 64.7 | 25.2 |

COMPARATIVE EXAMPLE 7

The same procedure as in Comparative Example 5 was repeated except that the potassium acetate was replaced by 22.5 mmol of potassium pivalate. The results of analyses are shown in Table 6.

EXAMPLE 11

The same procedure as in Example 9 was repeated except that the tetra-n-butylphosphonium acetate was replaced by 22.5 mmol of tetra-n-butylphosphonium pivalate. The results of analyses are shown in Table 6.

TABLE 6

| Example | r(DMC) [mmol/L·h] | r(CO2) [mmol/L·h] | S(CO2) (%) |
| --- | --- | --- | --- |
| Comparative Example 7 | 288 | 86.2 | 23.0 |
| Example 10 | 136 | 21.1 | 13.4 |

EXAMPLE 12

In a jacketed flask equipped with a stirrer and condenser were placed 221 ml of methanol, 3.7 mmol of palladium bromide, 16.4 mmol of cuprous bromide, 7.5 mmol of potassium bromide, 22.5 mmol of potassium acetate, and 15.5 mmol of duroquinone. Reaction was carried out at 60° C. for 6 hour while carbon monoxide and oxygen were being introduced into the flask at normal pressure and a flow rate of 8.0 liters/hour and 4.0 liters/hour, respectively.

The analysis of liquid product by gas chromatography indicates the formation of 256.6 mmol of dimethyl carbonate. The reaction after 6 hours formed 147.6 mmol of carbon dioxide, which is equal to 36.5% of the total amount of dimethyl carbonate and carbon dioxide formed.

COMPARATIVE EXAMPLE 8

The same procedure as in Example 12 was repeated except that the duroquinone was not added. The reaction formed 238.7 mmol of dimethyl carbonate and 250.8 mmol of carbon dioxide. The percentage of carbon dioxide formed as a by-product was 51.2%.

EXAMPLE 13

The same procedure as in Example 12 was repeated except that the duroquinone was replaced by 2.2 mmol of p-benzoquinone. The reaction formed 148 1 mmol of dimethyl carbonate and 57.0 mmol of carbon dioxide The percentage of carbon dioxide formed as a by-product was 27.8%.

EXAMPLE 14

The same procedure as in Example 12 was repeated except that the duroquinone was replaced by 15.5 mmol of 2-tertbutylanthraquinone. The reaction formed 141.2 mmol of dimethyl carbonate and 49.1 mmol of carbon dioxide. The percentage of carbon dioxide formed as a by-product was 25.8%.

EXAMPLE 15

The same procedure as in Example 12 was repeated except that the duroquinone was replaced by 15.5 mmol of phenanthraquinone. The reaction formed 199.6 mmol of dimethyl carbonate and 108.3 mmol of carbon dioxide. The percentage of carbon dioxide formed as a by-product was 35.2%.

EXAMPLE 16

The same procedure as in Example 12 was repeated except that the duroquinone was replaced by 2.2 mmol of hydroquinone. The reaction formed 105.6 mmol of dimethyl carbonate and 49.9 mmol of carbon dioxide. The percentage of carbon dioxide formed as a by-product was 32.1%.

What is claimed is:

1. In a process for preparing a carbonic acid ester which comprises, in a reaction system, reacting an alcohol with carbon monoxide and oxygen in the presence of a copper compound together with a platinum group metal compound and a reaction accelerator, the improvement which comprises: employing a solvent or mixture of solvents selected from the group consisting of nitriles and amides and, optionally, a quaternary phosphonium compound for a mixture of quaternary phosphonium compounds as a reaction accelerator selected from the group consisting of quaternary phosphonium halides, quaternary phosphonium weak acid salts and quaternary phosphonium alkoxides and mixtures thereof, said quaternary phosphonium halide having the formula (1)

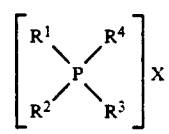

(1)

wherein $R^1$, $R^2$, $R^3$ and $R^4$ may be the same or different and denote alkyl groups, alkoxyl groups, aryl groups, aryloxy groups, substituted alkyl groups, substituted alkoxy groups, substituted aryl groups and substituted aryloxy groups and X is a halogen anion; and quaternary phosphonium weak acid salt having the formula (2)

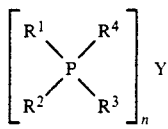

wherein $R^1$, $R^2$, $R^3$ and $R^4$ are as defined above, Y is an anion of a carboxylic or carbonic acid and n is a numeral equal to the valence of the anion of the carboxylic or carbonic acid; and said quaternary phosphonium alkoxide having the formula (3)

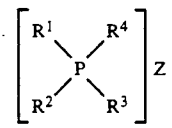

wherein $R^1$, $R^2$, $R^3$ and $R^4$ are as defined above and Z is an alkoxy group.

2. A process as claimed in claim 1 in which said solvent is selected from the group consisting of benzonitrile, isobutyronitrile, N,N-dimethylformamide and N,N-dimethylacetamide.

3. The process of claim 1, in which the nitrile compound is one or more members selected from the group consisting of benzonitrile and isobutyronitrile and the amide compound is one or more members selected from the group consisting of N,N-dimethylformamide and N,N-dimethylacetamide.

4. In a process for preparing a carbonic acid ester which comprises, in a reaction system, reacting an alcohol with carbon monoxide and oxygen in the presence of a copper compound along or a copper compound together with a platinum group metal compound and a reaction accelerator, the improvement which comprises: employing a reaction accelerator which consists essentially of a quaternary phosphonium halide and a member selected from the group consisting of quaternary phosphonium weak acid salts and quaternary phosphonium alkoxides, said quaternary phosphonium halide having the formula (1)

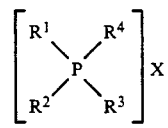

wherein $R^1$, $R^2$, $R^3$ and $R^4$ may be the same or different and denote alkyl groups, alkoxyl groups, aryl groups, aryloxy groups, substituted alkyl groups, substituted alkoxy groups, substituted aryl groups and substituted aryloxy groups and X is a halogen anion; said quaternary phosphonium weak acid salt having the formula (2)

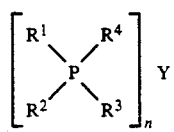

wherein $R^1$, $R^2$, $R^3$ and $R^4$ are as defined above, Y is an anion of a carboxylic or carbonic acid and n is a numeral equal to the valence of the anion of the carboxylic or carbonic acid; and said quaternary phosphonium alkoxide having the formula (3)

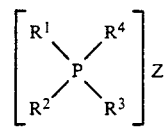

wherein $R^1$, $R^2$, $R^3$ and $R^4$ are as defined above and Z is an alkoxy group, said reaction system optionally containing a quinoid compound or a compound which is converted to a quinoid compound under the conditions of the reaction.

5. The process of claim 4, in which the platinum group metal compound is a palladium compound.

6. The process of claim 4, in which the alcohol has from 1 to 20 carbon atoms.

7. The process of claim 4, in which the alcohol is methanol.

8. The process of claim 4, in which the reaction system contains a quinoid compound or a compound that will be converted into a quinoid compound during the reaction.

9. The process of claim 4, in which said quaternary phosphonium halide is selected from the group consisting of [(n-$C_4H_9$)$_4$P]Cl, [(n-$C_4H_9$)$_3$$CH_3$P]Cl, [(n-$C_3H_7$)$_4$P]Cl, [(n-$C_4H_9$)$_4$P]Br and [(n-$C_3H_7$)P]Br, said quaternary phosphonium weak acid salt is selected from the group consisting of

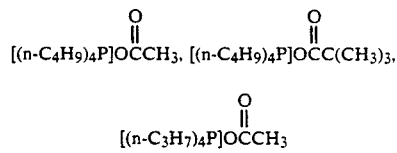

and [(n-$C_4H_9$)$_4$P]$_2$$CO_3$ and said quaternary phosphonium alkoxide is selected from the group consisting of [(n-$C_4H_9$)$_4$P]$OCH_3$ and [(n-$C_4H_9$)$_4$P]$OC_2H_5$.

10. In a process for preparing a carbonic acid ester which comprises, in a reaction system, reacting an alcohol with carbon monoxide and oxygen in the presence of a copper compound alone or a copper compound together with a platinum group metal compound and a reaction accelerator, the improvement which comprises: carrying out the reaction in the presence of a quinoid compound or a compound which is converted to a quinoid compound under the conditions of the reaction and, optionally, a quaternary phosphonium compound as a reaction accelerator selected from the group consisting of a quaternary phosphonium halides, quaternary phosphonium weak acid salts and quaternary phosphonium alkoxides, said quaternary phosphonium halide having the formula (1)

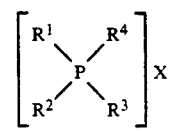

wherein $R^1$, $R^2$, $R^3$ and $R^4$ may be the same or different and denote alkyl groups, alkoxyl groups, aryl groups, aryloxy groups, substituted alkyl groups, substituted alkoxy groups, substituted aryl groups and substituted aryloxy groups and X is a halogen anion; said quaternary phosphonium weak acid salt having the formula (2)

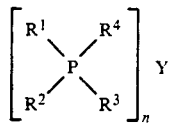

wherein $R^1$, $R^2$, $R^3$ and $R^4$ are as defined above, Y is an anion of a carboxylic or carbonic acid and n is a numeral equal to the valence of the anion of the carboxylic or carbonic acid; and said quaternary phosphonium alkoxide having the formula (3)

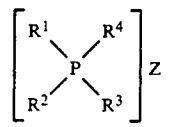

wherein $R^1$, $R^2$, $R^3$ and $R^4$ are as defined above and Z is an alkoxy group.

11. A process as claimed in claim 10 in which said quinoid compound is selected from the group consisting of unsubstituted and substituted ortho- and para-benzoquinones; polynuclear quinones selected from the group consisting of anthraquinone, 2-tert-butylanthraquinone and phenanthraquinone; and imino derivatives thereof, and said compound which is converted to said quinoid compound under the conditions of the reaction is selected from the group consisting of ketals of said quinoid compounds and hydrogenated compounds of said quinone compounds.

12. A process as claimed in claim 10 in which said quinoid compound is selected from the group consisting of duroquinone, p-benzoquinone, 2-ter-butylanthraquinone, phenanthraquinone and hydroquinone.

13. A process of claim 10, in which said quinoid compound or said compound that is converted into the quinoid compound in the reaction system is added in an amount of 0.1 to 5 wt. % based on the total weight of the reaction mixture.

14. The process of claim 10, in which the reaction system contains a copper compound together with a platinum group metal compound.

15. The process of claim 10, in which the alcohol has from 1 to 20 carbon atoms.

16. The process of claim 10, in which the alcohol is methanol.

* * * * *

UNITED STATES PATENT AND TRADEMARK OFFICE
CERTIFICATE OF CORRECTION

PATENT NO. : 5,089,650

DATED : February 18, 1992

INVENTOR(S) : Shigeru Yokota, et al

It is certified that error appears in the above-identified patent and that said Letters Patent is hereby corrected as shown below:

Column 8, line 46; change "for" to --or--.
          line 66; change "and" (second occurrence) to --said--.

Column 9, line 35; change "along" to --alone--.

Column 10, line 54; change "a quaternary" to --quaternary--.

Column 12, line 13; change "ter" to --tert--.

Signed and Sealed this

Twenty-first Day of September, 1993

Attest:

BRUCE LEHMAN

*Attesting Officer*     *Commissioner of Patents and Trademarks*